United States Patent
Carbone et al.

(10) Patent No.: US 6,923,075 B2
(45) Date of Patent: *Aug. 2, 2005

(54) METHODS FOR SAMPLING AND TESTING DATA CENTERS FOR METALLIC PARTICULATES

(75) Inventors: Ralph A. Carbone, Roseville, CA (US); David J. Roche, Folsom, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/658,510

(22) Filed: Sep. 8, 2003

(65) Prior Publication Data

US 2004/0045377 A1 Mar. 11, 2004

Related U.S. Application Data

(63) Continuation of application No. 09/846,620, filed on May 1, 2001, now Pat. No. 6,651,521.

(51) Int. Cl.$^7$ ................................................. G01N 1/00
(52) U.S. Cl. .................................................. 73/864.71
(58) Field of Search ........................ 73/864.71, 864.81, 73/864.91; 250/428

(56) References Cited

U.S. PATENT DOCUMENTS

| | | | |
|---|---|---|---|
| 3,074,276 A | | 1/1963 | Moos |
| 4,805,468 A | | 2/1989 | Choudhry |
| 5,373,748 A | | 12/1994 | Lioy et al. |
| 5,851,285 A | * | 12/1998 | Johnsson et al. .............. 117/87 |
| 6,021,681 A | | 2/2000 | Jezek |
| 6,040,077 A | | 3/2000 | Debe et al. |
| 6,651,521 B2 | * | 11/2003 | Carbone et al. ......... 73/864.71 |

* cited by examiner

*Primary Examiner*—Robert Raevis

(57) ABSTRACT

The present invention is drawn to methods for sampling and/or testing for the presence of whisker-like metallic particulates in data centers or computer rooms. For example, a method for discovering the presence of an undesired whisker-like metallic particulate in a data center is disclosed comprising providing a tool having a conductive adhesive portion wherein the conductive adhesive portion is capable of capturing and retaining the whisker-like metallic particulates in their fragile condition, locating a surface of the data center where metallic particulates may be present, extracting from the surface any whisker-like metallic particulates present in substantially their fragile condition using the tool, and confirming with an electron microscope whether or not any whisker-like metallic particulates are present on the conductive adhesive portion of the tool.

23 Claims, No Drawings

METHODS FOR SAMPLING AND TESTING DATA CENTERS FOR METALLIC PARTICULATES

PRIOR APPLICATION

This is a continuation of application Ser. No. 09/846,620, filed in the U.S. patent office on May 01, 2001 now U.S. Pat. No. 6,651,521.

FIELD OF THE INVENTION

The present invention is drawn to methods for sampling and/or testing data centers or computer rooms for fragile whisker-like metallic particulates.

BACKGROUND OF THE INVENTION

For many years, the electronics industry has been aware of the threat posed by zinc whisker or zinc needle growth on zinc-electroplated surfaces. As technology has advanced, and processors, power sources, and the like have become increasingly smaller, a growing concern has developed with respect to these whisker-like conductive contaminants. This has been particularly a problem in the so-called "computer room" where zinc electroplated floor tiles are used to form grounds for computer components, as well as provide a convenient path for technicians to run cables and wires. On the bottom of some of these floor tiles, as well as in other locations, these whisker-like growths can form.

Generally, it is known that tin, zinc, and cadmium plating can grow whiskers. This type of plating is frequently used as corrosion protection for steel electronic enclosures. Some have proposed that certain electroplating processes impart internal stress in these metals, setting the stage for whisker growth. Though tin is more susceptible to whisker formation than either cadmium or zinc, zinc plating is more common in computer rooms and data center. This is because zinc plating is often applied to electronic enclosures, structural elements, and other equipment made of high strength, low alloy steel. Zinc whiskers are formed from metal surfaces coated with zinc in a galvanization process to help protect them from corrosion. The zinc whiskers generally can be described as zinc filaments extending from these treated surfaces. They are normally only a few microns in width, but can be several hundred to over a thousand microns in length.

The first zinc-plated enclosures in use with computer equipment presented some whisker problems, but these problems were easily remedied due to the large circuitry spacing and higher voltages used in the systems. However, as technology has become more sophisticated, zinc whiskers are creating a greater problem. For example, low voltages as are present in more modern systems are not capable of burning off metallic whiskers in a quick manner. It is also suspected that higher operating temperatures of systems as a whole encourage the incubation and growth of whisker-like particulates.

Zinc whisker growth has been found on sub-racks, switches, card cages, floor tiles, frames, internet routers, and other electroplated surfaces. They can also be found growing from certain computer hardware. However, if these whisker-like particulates become airborne, they can be found anywhere in a computer room or computer data center, or can be carried into a data center from an external source. Not all electroplated surfaces appear to exhibit whisker growth, and not all of such surfaces develop the problem at the same rate. Thus, it is suspected that whisker growth is affected to some extent by the environment in combination with the electroplated surface.

As previously stated, floor tiles are a location where zinc whisker growth is particularly prevalent. This is partly because these floor tiles have large surface areas, and are often disturbed during normal activity in a computer room or data center, e.g., removed by technicians or disturbed by running cable, etc. Additionally, raised floor tile construction used in most computer rooms is utilized as a duct for supplying necessary airflow to computer components. Because of this activity and airflow, zinc whiskers can easily be dislodged and carried to the hardware. Additionally, floor tiles are often dragged across the top of each other as they are removed from a floor grid, spreading tile contamination throughout the room.

A reason that zinc whiskers (or other undesired metallic particulates) cause failures or other problems in computer rooms is because they are conductive contaminants, and can actually cause shorts on circuit board cards, power supplies, or other electronic components. As computer circuitry has become smaller, and voltages have decreased generally, short metallic whiskers can span two electrically isolated features on a circuit board. Such a span can, for example, misdirect current causing unforeseen problems. Though the growth of zinc whiskers is not new, their ability to impact hardware reliability has been increased by denser geometries of the newer technologies.

Metallic particulates such as zinc whiskers have been discovered by visual inspection and/or by the wiping of an area with a swatch. Thus, in the prior art, the presence of zinc whiskers in data centers have been discovered using less precise methods than those of the present invention. Some of these prior art methods do not provide the detailed information sometimes necessary for determining the best approach for remediation. For example, with respect to wipe sampling, a wet wipe is used to sample an area. The wipe can then be sealed in a plastic bag and sent to an environmental lab where tests are conducted to determine whether zinc is present on the wipe. However, with this method, tile lab is not always able to determine if the zinc is in the form of a zinc whisker. Further, even if such a determination can be made, tile lab may not be able to accurately determine of the zinc whisker, the surface properties of the zinc whisker, or the concentration of zinc whiskers sampled from a given area.

SUMMARY OF THE INVENTION

The present inventors have determined that providing a method of sampling and/or testing for the presence of fragile whisker-like metallic particulates in a data center, while maintaining the sample in its fragile state, would be an advancement in the art. Thus, the present invention is drawn to methods for sampling and/or testing data centers or computer rooms for the presence of fragile whisker-like metallic particulates in a data center. A first method of sampling for the presence of fragile whisker-like metallic particulates in a data center is disclosed. There tile sampling steps comprise providing a tool capable of capturing and retaining the whisker-like metallic particulates in their fragile condition, locating a surface of the data center where metallic particulates may be present, and extracting from the surface any whisker-like metallic particulates present in their substantially fragile condition.

Additionally, a method for discovering the presence of an undesired whisker-like metallic particulate in a data center is disclosed comprising locating a surface of the data center where the presence of a whisker-like metallic particulate is suspected, extracting any whisker-like metallic particulate that may be present on the surface onto an adhesive intermediate substrate, and confirming whether or not any whisker-like metallic particulates are present on the adhesive intermediate substrate.

In a more detailed aspect of the invention, a method for discovering the presence of an undesired whisker-like metallic particulate in a data center is disclosed. This method comprises the steps of providing a tool having a conductive adhesive portion wherein the conductive adhesive portion is capable of capturing and retaining the whisker-like metallic particulates in their fragile condition, locating a surface of the data center where metallic particulates may be present, extracting from the surface any whisker-like metallic particulates present in substantially their fragile condition using the tool, and confirming with an electron microscope whether or not any whisker-like metallic particulates are present on the conductive adhesive portion of the tool.

DETAILED DESCRIPTION OF THE INVENTION

Before the present invention is disclosed and described, it is to be understood that this invention is not limited to the particular process steps and materials disclosed herein because such process steps and materials may vary somewhat. It is also to be understood that the terminology used herein is used for the purpose of describing particular embodiments only. The terms are not intended to be limiting because the scope of the present invention is intended to be limited only by the appended claims and equivalents thereof.

It must be noted that, as used in this specification and the appended claims, the singular forms "a," "an," and "the" include plural referents unless the content clearly dictates otherwise.

"Data center" or "computer room" is intended to include any room where a substantial amount of computer equipment is present, such as, for example, an internet server room or a large company computer room.

"Whisker-like metallic particulate" includes any metal particulate growth that is elongated along an axis. Typically, these particulates grow from electroplated metal surfaces, and can break off becoming mobile. Zinc, tin, and cadmium plating can form these whiskers, though any other plated metal may also form whisker-like protrusions under the right conditions.

"Adhesive" shall include any material that provides more adhesive strength than the adhesion provided by water on a cloth or paper material (such as with a wet wipe), and are preferably substantially more adhesive. Additionally, it is preferred that the adhesive substance he a material not significantly prone to evaporative tendencies over short periods of time. Examples of adhesives can include materials used for glues and tapes. An adhesive carbon conductive material can also be used.

With these definitions in mind, several methods are disclosed herein that are effective for sampling and/or testing for the presence of whisker-like metallic particulates, including, for example, zinc whiskers. With respect to a first method, a method of sampling for the presence of fragile whisker-like metallic particulates in a data center is disclosed. This method comprises the steps of providing a tool capable of capturing and retaining the whisker-like metallic particulates in their fragile condition, locating a surface of the data center where metallic particulates may be present, and extracting from the surface any whisker-like metallic particulates present in substantially their fragile condition.

With this method, the tool can comprise an adhesive portion for extracting the whisker-like metallic particulates. Additionally, the adhesive portion can be a conductive material such as, for example, a carbon conductive material. One reason that it may be desirous to use a conductive material is because if any analysis of the sample is to occur with the aid of an electron microscope, then there need not be additional preparation required to view the sample. If, for example, a cellophane adhesive was used to extract the sample, then an intermediate step of carefully transferring the sample to a conductive substrate would be required prior to electron microscope viewing, though such an embodiment is also within the scope of the invention.

One technique that can be used to extract a sample from a surface can include gently pressing an adhesive portion of a tool on the surface to be sampled. Further, it may be desired to extract the sample such that a density of the whisker-like metallic particulates over a predetermined surface area can be determined. If the desire is simply to determine whether or not zinc whiskers are present in a data center or computer room, then any area can be sampled. However, for a more controlled analysis, the location(s) of the sample(s) taken from the room should be recorded.

Once the surface is sampled, a further step of protecting the sample from substantial contamination prior to testing the sample for the presence of whisker-like metallic particulates can be carried out. For example, one can take steps to ensure that the sample is stored in an enclosure such that the adhesive portion does not contact the enclosure. Such an enclosure can be a box having support structures for holding a handle portion of the tool, while suspending the adhesive portion within the box. Additionally, though not required, the tool can be configured to be modular such that the adhesive portion is removable from a handle portion. For example, the adhesive portion can be a conductive carbon adhesive in the shape of a disc that can be removed from an elongated handle portion of the tool. Thus, viewing of the conductive carbon adhesive with an electron microscope or other analytical equipment can occur without the presence of the handle. Though this method can be used to sample any fragile whisker-like metallic particulate, typically, these particulates are selected from the group consisting of zinc whiskers, tin whiskers, and cadmium whiskers. If sampling a computer room or data center, a typical place that one might sample is a floor tile surface, particularly, the bottom of a floor tile.

If a more thorough sampling is necessary, additional sampling steps can be taken. Such steps can include locating a second surface of the data center wherein whisker-like metallic particulates may be present, providing a second tool capable of capturing and retaining the whisker-like metallic particulates in their fragile condition, and extracting from the second surface any whisker-like metallic particulates present in their substantially fragile condition.

Alternatively, a method for discovering the presence of an undesired whisker-like metallic particulate in a data center is also disclosed. With this method, several steps can be carried out including locating a surface of the data center where the presence of a whisker-like metallic particulate is suspected, extracting any whisker-like metallic particulate that may be present on the surface onto an adhesive intermediate substrate, and confirming whether or not any whisker-like metallic particulates are present oil the intermediate substrate.

Though not required, in this embodiment, it is preferred that the step of extracting any whisker-like metallic particulates is done such that the particulates are substantially retained in their fragile condition. Again, if the desire is to use an electron microscope to confirm or reject the presence of the whisker-like metallic particulates, the intermediate substrate can be a conductive adhesive, such as a carbon conductive adhesive. If such a conductive adhesive is used, then an additional step of slide preparation for use with an electron microscope can be avoided. Appropriate electron microscopes that can be used include scanning electron microscopes, field emission electron microscopes, and transmission electron microscopes, to name a few.

If one is viewing whisker-like metallic particulates with an electron microscope (or other microscopic viewing device), then the step of characterizing any particulates present with respect to geometry, surface properties, and/or density can be carried out. This can be done to provide more information to an analyst regarding the particulates present in a data center or computer room. In addition, the whisker-like metallic particulates can also be characterized using energy dispersive spectroscopy (EDS). One reason that the use of carbon conducive material is a good material for use during sampling of the computer room or data center is that it provides peaks (carbon) that do not interfere with zinc peaks if EDS is used for analysis of the sample.

In another more detailed aspect of the invention, a method for discovering the presence of an undesired whisker-like metallic particulate in a data center is disclosed comprising the steps of providing a tool having a conductive adhesive portion wherein the conductive adhesive portion is capable of capturing and retaining the whisker-like metallic particulates in their fragile condition, locating a surface of the data center where metallic particulates may be present, extracting from the surface any whisker-like metallic particulates present in their substantially fragile condition using the tool, and confirming with an electron microscope whether or not any whisker-like metallic particulates are present on the conductive adhesive portion of the tool. Optionally, the step of characterizing any whisker-like metallic particulates confirmed to be present for geometry, surface properties, and density can also be carried out. If the tool is modular, the conductive adhesive portion can be removed from the tool prior to the step of confirming the presence of metallic particulates.

Though the methods of the present invention are drawn primarily to the sampling, detection, and characterization of whisker-like metallic particulates, if such particulates are discovered, then remediation steps should be taken. For example, if zinc whisker growth is identified on a floor tile, extreme caution should be exercised to avoid making the problem worse, e.g., spreading the zinc whiskers throughout the data center or computer room. One remediation approach is to replace all floor tiles, with selective encapsulation of inaccessible tiles. This procedure can be an extremely delicate and labor-intensive procedure, and if not done properly, can cause the problem to become worse through inadvertent spreading. If a floor tile or raised floor is grossly contaminated, then a detailed plan may be necessary to reduce the likelihood of increased problems associated with remediation. For example, areas of greatest contamination should be identified using the methods of the present invention. Then, with this knowledge, appropriate equipment can be moved or affected areas can be isolated from affected areas. In any event, care should be taken not to disturb any loose whiskers during remediation cleanup.

An example of several remediation steps that can be taken are described herein. First, all equipment that can be powered down and removed from the data center should be removed. Next, as many air conditioning units that can be powered down should also be powered down. The remaining equipment can then be covered with plastic barrier tents, such as, for example, between the ceiling and the floor. If there is still airflow under the floor, under-floor barriers can also be created. This is an important step as these barriers will protect the equipment from zinc-laden airflow during the replacement process. The affected panels can now more safely be carefully lifted and removed from the room. This should be done without sliding or otherwise shaking the tiles. Once the panels are safely within plastic bags, they can be removed from the room. The under-floor area can be cleaned with a vacuum, wet wiping, or other known procedures. New panels (not subject to whisker-like metallic growth) can now be put in place and the room restored to its original condition.

While the invention has been described with reference to certain preferred embodiments, those skilled in the art will appreciate that various modifications, changes, omissions, and substitutions can be made without departing from the spirit of the invention. It is therefore intended that the invention be limited only by the scope of the appended claims.

We claim:

1. A method of sampling for the presence of fragile whisker-like metallic particulates in a data center comprising:
    (a) providing a tool capable of capturing and retaining the whisker-like metallic particulates in their fragile condition including a whister-like geometry, wherein the tool comprises an adhesive portion having adhesion strength greater than water for extracting the whisker-like particulates;
    (b) locating a surface of the data center where metallic particulates may be present; and
    (c) extracting from the surface any whisker-like metallic particulates present in substantially their fragile condition and in a manner enabling characterization of the whisker-like geometry.

2. A method as in claim 1 wherein the tool comprises an adhesive portion for extracting the whisker-like metallic particulates.

3. A method as in claim 2 wherein the adhesive portion is a conductive adhesive.

4. A method as in claim 3 wherein the conductive adhesive is a carbon conductive material.

5. A method as in claim 2 wherein the step of extracting is carried out by pressing the adhesive portion on the surface.

6. A method as in claim 1 wherein the step of extracting further comprises sampling a density of the whisker-like metallic particulates over a predetermined surface area.

7. A method as in claim 1 further comprising the step of recording a location of the surface.

8. A method as in claim 1 further comprising the step of storing a sample such that the sample is protected from substantial contamination.

9. A method as in claim 8 wherein the sample is stored in an enclosure such that the adhesive portion does not contact the enclosure.

10. A method as in claim 2 wherein the tool is modular and the adhesive portion is removable from a handle portion.

11. A method as in claim 1 wherein the fragile whisker-like metallic particulates are selected from the group consisting of zinc whiskers, cadmium whiskers, tin whiskers, and aluminum whiskers.

12. A method as in claim 1 further comprising the steps of:
    (a) locating a second surface of the data center wherein whisker-like metallic particulates may be present;

(b) providing a second tool capable of capturing and retaining the whisker-like metallic particulates in their fragile condition including a whisker-like geometry, wherein the second tool comprises an adhesive portion having adhesion strength greater than water for extracting the whisker-like particulates; and (c) extracting from the second surface any whisker-like metallic particulates present in substantially their fragile condition and in a manner enabling characterization of the whisker-like geometry.

13. A method as in claim 1 wherein the surface is on a floor tile.

14. A method as in claim 13 wherein the step of extracting is from a bottom side of the floor tile.

15. A method for discovering a presence of an undesired whisker-like metallic particulate in a data center comprising:

(a) locating a surface of the data center where the presence of a whisker-like metallic particulate having a whisker-like geometry is suspected;

(b) extracting any whisker-like metallic particulate that may be present on the surface onto an adhesive intermediate substrate in a manner enabling characterization of the whisker-like geometry, wherein the adhesive intermediate substrate provides an adhesion strength greater than water for extracting the whisker-like particulates; and (c) confirming whether or not any whisker-like metallic particulates are present on the adhesive intermediate substrate.

16. A method as in claim 15 wherein the step of extracting any whisker-like metallic particulates is done such that the whisker-like metallic particulates are substantially retained in their fragile condition.

17. A method as in claim 15 wherein the adhesive intermediate substrate is conductive.

18. A method as in claim 17 wherein the intermediate substrate comprises conductive carbon.

19. A method as in claim 17 wherein the step of confirming whether or not any whisker-like metallic particulates are present is done with an electron microscope.

20. A method as in claim 19 wherein the electron microscope is selected from the group consisting of a scanning electron microscope, a field emission electron microscope, and a transmission electron microscope.

21. A method as in claim 15 wherein the whisker-like metallic particulates are selected from the group consisting of zinc whiskers, tin whiskers, cadmium whiskers, aluminum whiskers, and combinations thereof.

22. A method as in claim 15 wherein the step of confirming whether or not any whisker-like metallic particulates are present further comprises the step of characterizing any whisker-like metallic particulates present with respect to geometry, surface properties, and density.

23. A method as in claim 15 further comprising the step of characterizing the whisker-like metallic particulates using energy dispersive spectroscopy (EDS).

* * * * *